United States Patent
Sorensen

(10) Patent No.: US 11,998,666 B2
(45) Date of Patent: Jun. 4, 2024

(54) OCCUPANT RESPIRATION ISOLATION METHOD

(71) Applicant: International Truck Intellectual Property Company, LLC, Lisle, IL (US)

(72) Inventor: Tom Lee Sorensen, Naperville, IL (US)

(73) Assignee: International Truck Intellectual Property Company, LLC, Lisle, IL (US)

( * ) Notice: Subject to any disclaimer, the term of this patent is extended or adjusted under 35 U.S.C. 154(b) by 632 days.

(21) Appl. No.: 17/158,271

(22) Filed: Jan. 26, 2021

(65) Prior Publication Data

US 2022/0080078 A1    Mar. 17, 2022

Related U.S. Application Data

(60) Provisional application No. 63/079,770, filed on Sep. 17, 2020.

(51) Int. Cl.
  *A61L 9/20* (2006.01)
  *B60N 2/56* (2006.01)

(52) U.S. Cl.
  CPC ............... *A61L 9/20* (2013.01); *B60N 2/56* (2013.01); *A61L 2209/111* (2013.01); *A61L 2209/12* (2013.01)

(58) Field of Classification Search
  CPC .......... B60D 13/00; B60D 13/06; B60N 2/00; B60N 2/56; B60N 2/5621; B60N 2/5635; B60N 2/565; B60N 2/5657; A61L 9/20; A61L 2209/111; A61L 2209/12
  See application file for complete search history.

(56) References Cited

U.S. PATENT DOCUMENTS

| | | | |
|---|---|---|---|
| 2008/0283663 A1* | 11/2008 | Space | B64D 13/06 244/118.5 |
| 2014/0179212 A1* | 6/2014 | Space | B60N 2/5635 454/76 |
| 2018/0118351 A1* | 5/2018 | Fox | G01N 33/0047 |

(Continued)

FOREIGN PATENT DOCUMENTS

| | | |
|---|---|---|
| EP | 3 466 815 | 10/2019 |
| WO | WO-2021263094 A1 * | 12/2021 |

*Primary Examiner* — Kevin Joyner
*Assistant Examiner* — Justin Hwang
(74) *Attorney, Agent, or Firm* — Mark C. Bach; Umang Khanna

(57) ABSTRACT

A method of isolating vehicle occupant respiration includes energizing a source of ultraviolet radiation to sterilize in air. A first sensor detects carbon dioxide content of that air. A second sensor detects quality of that air. A third sensor detects particulate in that air. Result from the first sensor is compared to baseline carbon dioxide reading recorded in a controller connected with the sensors. Fan speed increases temporal duration of air exposure to ultraviolet radiation. Result from the second sensor is compared with baseline air quality recorded in the controller. A signal is sent to a display comprising the filtration system to identify contaminate in the air. Result from the third sensor is compared with baseline particulate recorded in controller. An alert is sent to an interested party indicating particulate presence in the air.

4 Claims, 3 Drawing Sheets

(56) References Cited

U.S. PATENT DOCUMENTS

| | | |
|---|---|---|
| 2018/0264160 A1 | 9/2018 | Benedek et al. |
| 2020/0223292 A1* | 7/2020 | Kazyak .............. B60H 1/00292 |
| 2022/0054699 A1* | 2/2022 | Nakama ................. F24F 7/003 |

* cited by examiner

OCCUPANT RESPIRATION ISOLATION METHOD

REFERENCE TO RELATED APPLICATIONS

This patent applications claims benefit of U.S. provisional patent Application No. 63/079,770 filed on Sep. 17, 2020. That patent application is incorporated herein in its entirety by this reference.

BACKGROUND

Currently, there are concerns about an occupant of a vehicle being exposed to less than favorable, such as containing a contaminant, low oxygen concentration and the like, air within the vehicle. Accordingly, it is desirable to have a system and a method for effectively filtering and isolating respiration of an occupant of vehicle.

SUMMARY

This disclosure relates to embodiments of a system and a method for isolating respiration of a vehicle occupant. According to one embodiment, an occupant respiration isolation system comprises a plenum having an interior. A source of ultraviolet radiation is located in the interior. A first duct is disposed between an interior of a vehicle and the interior of the plenum for conveying air from the interior of the vehicle to the interior of the plenum. A vent is disposed between the interior of the vehicle and the first duct allowing air from the interior of the vehicle to enter the first duct. A fan is operatively connected with the plenum that varies airflow through the plenum. A third duct conveys air from the interior of the plenum to the interior of the vehicle. A first sensor generating a first signal is disposed in the interior of the plenum. A controller is disposed on the vehicle operatively connected with the first sensor for receiving the first signal.

According to one embodiment, a method of isolating vehicle occupant respiration includes energizing a source of ultraviolet radiation to sterilize in air. A first sensor detects carbon dioxide content of that air. A second sensor detects quality of that air. A third sensor detects particulate in that air. Result from the first sensor is compared to baseline carbon dioxide reading recorded in a controller connected with the sensors. Fan speed increases temporal duration of air exposure to ultraviolet radiation. Result from the second sensor is compared with baseline air quality recorded in the controller. A signal is sent to a display comprising the filtration system to identify contaminate in the air. Result from the third sensor is compared with baseline particulate recorded in controller. An alert is sent to an interested party indicating particulate presence in the air.

DETAILED DESCRIPTION

Figure 1:
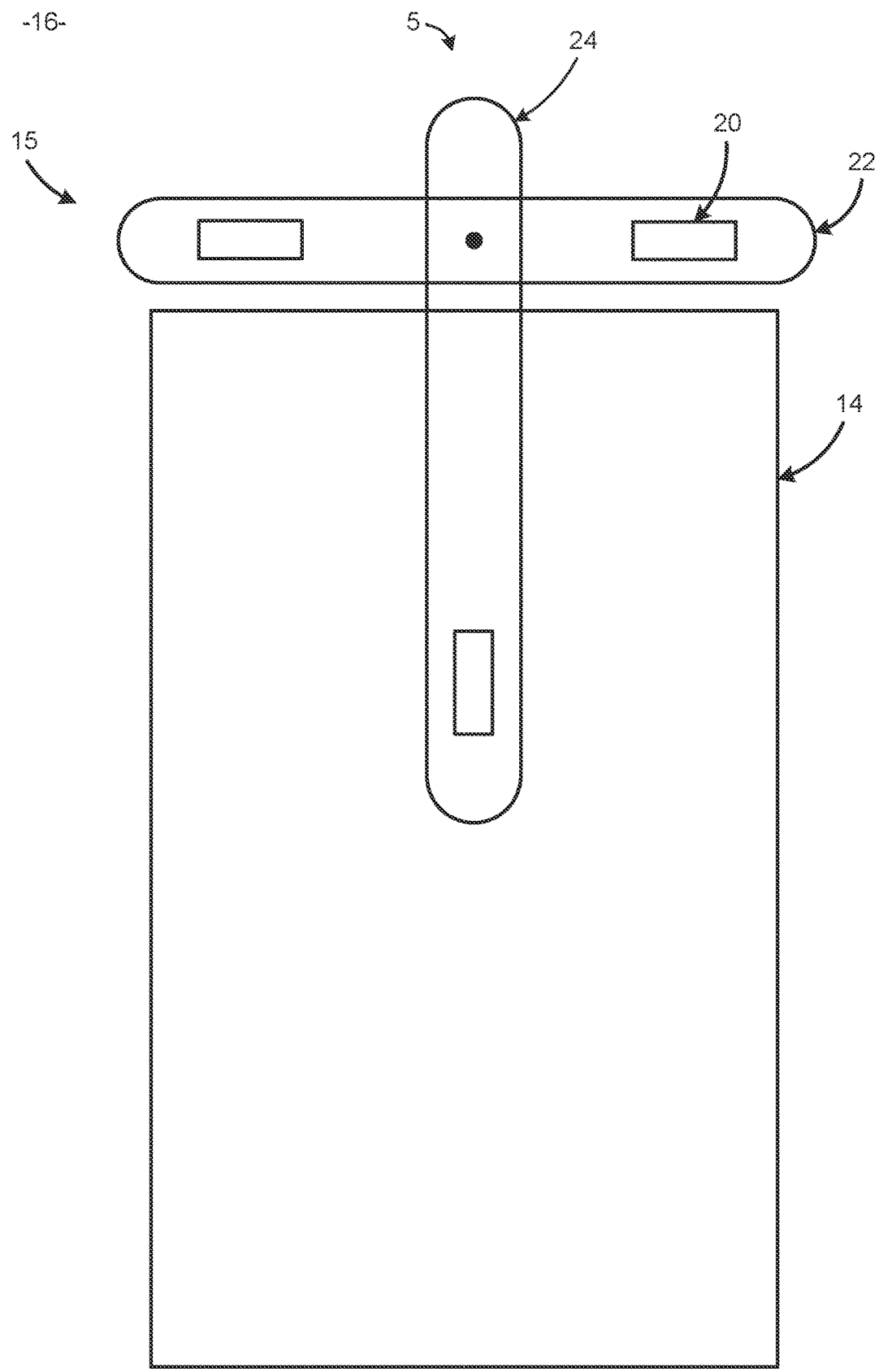
FIG. 1 is diagram of a portion of a vehicle having an occupant respiration isolation system described herein.

This disclosure relates specifically to a system 5 and a method for isolating and filtering respiration of an occupant of a vehicle 16, such as a school bus, a commercial vehicle and the like. As shown in FIG. 1, one embodiment disclosed herein generally comprises a filtration system 10 comprising a plenum 12 attached to a seat 14 for supporting an occupant disposed in an interior 15 of the vehicle 16. The system 5 for isolating and sterilizing respiration in the vehicle 16 includes at least one source 18 of ultraviolet radiation located in the plenum 12 of the filtration system 10. Other elements of the filtration system 10 include, but are not limited to, a vent 20 disposed between the interior 15 of the vehicle 16 and a first duct 22 allowing air from the interior 15 of the vehicle 16 to enter the first duct 22, the first duct 22 is disposed between the vent 20 and an interior 38 of the plenum 12 for conveying air between the vent 20 and the interior 38 of the plenum 12, a second duct 24 connected to plenum 12 positioned between a first occupant and a second occupant both located on seat 14 to separate air from the first occupant from air from the second occupant, a fan 26 operatively connected with the plenum that varies airflow through plenum 12, and a third duct 28, shown in FIG. 2, operatively connected with an interior 38 of the plenum 12 conveying air from an interior 38 of the plenum 12 to an interior 15 of the vehicle 16.

Figure 2:
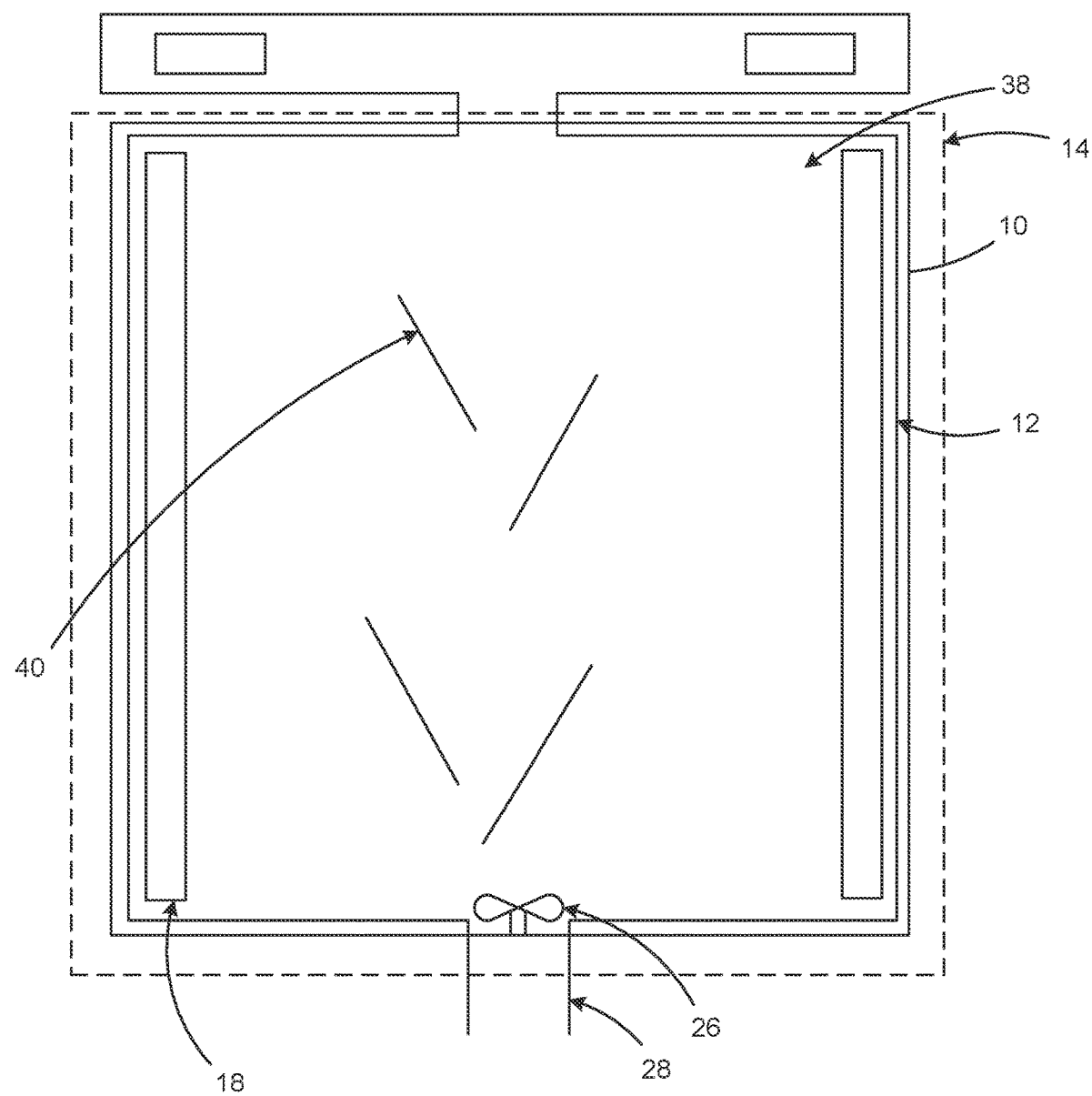
FIG. 2 is a diagram similar to FIG. 1 showing elements of the occupant respiration isolation system described herein.
Figure 3:
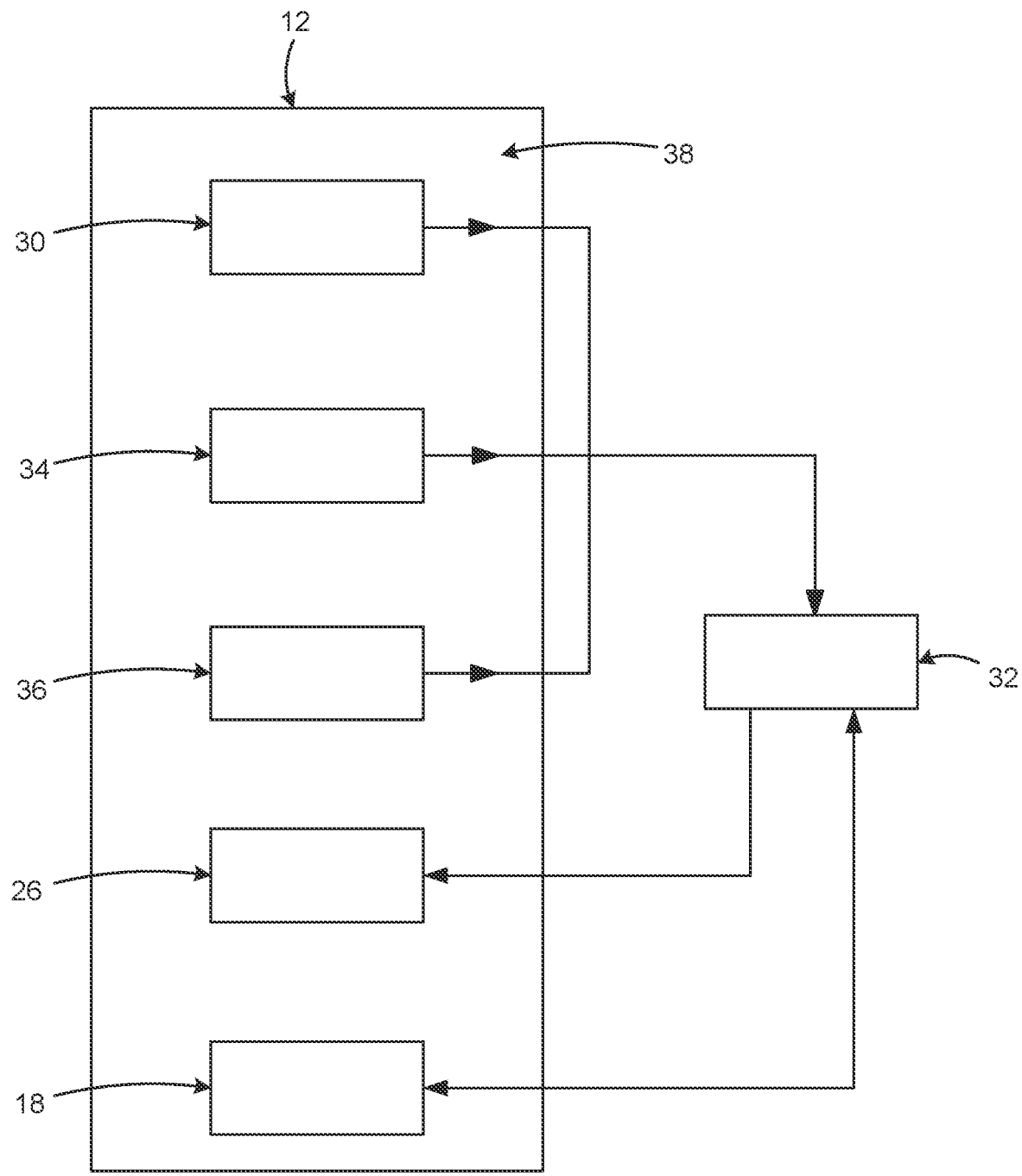
FIG. 3 is a diagram similar to FIG. 2 showing elements of the occupant respiration isolation system described herein.

As shown in FIGS. 2 and 3, at least one first sensor 30 is disposed on the interior 38 of plenum 12. In one embodiment, the at least one first sensor 30 samples air adjacent the at least one sensor 30 to detect carbon dioxide content of that air. The at least one first sensor 30 is connected, wired, wirelessly, or otherwise, to controller 32, which can compromise at least one data processor on the vehicle 16. In some embodiments, the at least one data processor on the vehicle 16 is supplemented by another at least one data processor located off the vehicle 16, such as another at least one data processor operatively connected with the at least one data processor on the vehicle 16 wirelessly. The controller 32 is suitably connected with fan 26, either wired or wirelessly.

At least one second sensor 34 is disposed on the interior 38 of plenum 12. The at least one second sensor 34 samples air adjacent to the at least one second sensor 34 to detect quality of that air including, but not limited to, presence of an airborne contaminant, such as carbon monoxide, carbon dioxide, diesel particulate, pollen, viruses, bacteria, a vapor, an aerosol and the like. The at least one second sensor 34 is connected, wired, wirelessly, or otherwise, to controller 32, which can compromise at least one data processor, on the vehicle 16.

Based on a first signal, indicative of at least one of carbon dioxide, air quality. carbon monoxide, carbon dioxide, diesel particulate, pollen, viruses, bacteria, vapor, aerosol and the like, provided by at least one of the at least one first sensor 30 and the at least one second sensor 34, the controller 32 provides a second signal to a display, controller, or any other element comprising the system 5 on the vehicle 16 as is appropriate. That second signal can alert an interested party, such as a user of the vehicle, a manager of the vehicle 16, and the like that contamination associated with air about the vehicle 16 has been detected. Presence of contamination can indicate many things, such as maintenance of the system 5 or the vehicle 16 is recommended and the like. In some embodiments, the controller 32 is augmented by at least one data processor located outside of the vehicle 16 and connected with the vehicle 16 by appropriate means, such as wireless connection to the internet and the like.

At least one third sensor 36 is disposed on the interior 38 of plenum 12. The at least one third sensor 36 samples air adjacent to the at least one third sensor 36 to detect a particulate in the air. The at least one third sensor 36 is connected, wired, wirelessly, or otherwise, to controller 32, which can compromise at least one data processor, on the vehicle 16. In some embodiments, the controller 32 is augmented by at least one data processor located outside of the vehicle 16 and connected with the vehicle 16 by appropriate means, such as wireless connection to the internet and the like. Depending on a third signal from the at least one third sensor 36, the controller 32 can provide an alert to a display, controller, any other element in the system 5 on the vehicle 16, and an interested party, as is appropriate, indicating presence of the particulate detected by the at least one third sensor 36.

In some embodiments, the at least one source 18 comprises at least one ultraviolet radiation lamp. The ultraviolet radiation has a wavelength within the range of about 100 nanometers to about 280 nanometers, with 265 nanometers being the peak wavelength to sanitize germicidal activity. The at least one source 18 is connected to the controller 32, either wired or wirelessly. The controller 32 is disposed on the vehicle 16. In some embodiments, the controller 32 comprises a body controller of a vehicle 16. The at least one source 18 are positioned within the filtration system 10 at locations empirically determined to sterilize air flowing through the filtration system 10 illuminated by the ultraviolet radiation from the at least one source 18.

In some embodiments, at least one baffle 40 is located within the interior 38 of the plenum 12.

As shown in FIG. 2, the at least one baffle 40 is positioned within the plenum 12 at locations empirically determined to increase surface area within the plenum 12 exposed to ultraviolet radiation from source 18. Some embodiments may include multiple at least one baffle 40, with four (4) at least one baffle 40 included in the embodiment shown in FIG. 2. The at least one baffle 40 is positioned to collect an item, such as a respiration droplet and the like, from air about the at least one baffle 40 and allow ultraviolet radiation from source 18 to sanitize a surface of the at least one baffle 40. Location of the at least one source 18 is chosen to reduce likelihood of unintended exposure to ultraviolet radiation from the at least one source 18, i.e. reduce likelihood of exposure of a vehicle 16 occupant to the ultraviolet radiation.

The controller 32 determines operation of the at least one source 18, namely when the at least one source 18 emits ultraviolet radiation. The controller 32 can determine intensity of the ultraviolet radiation. The controller 32 can be programmable. The controller 32 can allow the at least one source 18 to emit ultraviolet radiation, for instance, at specific times of day, for specific temporal duration, etc. The controller 32 may allow the at least one source 18 to emit ultraviolet radiation at specific times to manage vehicle power usage. In some embodiments, the controller 32 may allow the at least one source 18 to emit ultraviolet radiation substantially continuously thereby enabling substantially continuous sterilization of the filtration system 10.

With structure of embodiments of the system 5 for isolating and filtering respiration of an occupant of a vehicle being described, now attention is drawn to a method of isolating and sterilizing respiration from an occupant of a vehicle.

Once the vehicle 16 includes a filtration system 10 with at least one source 18 of ultraviolet radiation and a fan 26 located in a plenum 12 of filtration system 10, then temporal duration of emission of ultraviolet radiation from the at least one source 18 of ultraviolet radiation and intensity of that ultraviolet radiation, along with airflow intensity from the at least one fan 26, are determined.

The at least one first sensor 30 samples air inside the plenum 12 periodically for carbon dioxide and reports results to the controller 32. The controller 32 compares result from the at least one first sensor 30 to baseline carbon dioxide reading recorded in controller 32, thereby determining required fan 26 speed to increase air exposure to the at least one ultraviolet radiation source 18.

The at least one second sensor 34 samples air inside the plenum 12 periodically for air quality and reports results to the controller 32. The controller 32 compares result from the at least one second sensor 34 with baseline air quality recorded in the controller 32, thereby determining whether air meets the appropriate quality standard. The controller 32 sends the second signal to a display, controller, or any other element comprising the system 5 on the vehicle 16 as is appropriate.

The at least one third sensor 36 samples air inside the plenum 12 periodically for particulate and reports results to the controller 32. The controller 32 compares result from the at least one third sensor 36 with baseline particulate recorded in controller 32, thereby determining particulate quantity and providing the third signal to an interested party. In one embodiment, the interested party may be an operator of the vehicle 16 and the third signal may indicate location of a seat 14 associated with the particulate and potential next steps.

For instance, when a first occupant and a second occupant of a vehicle 16 sit in one seat 14, duct 24 can be articulated between the first occupant and the second occupant to separate air from first occupant from air from second occupant. While the duct 24 is between a first occupant and a second occupant, the at least one fan 26 in plenum 12 pulls air from a first occupant and a second occupant into plenum 12 through duct 24. The at least one source 18 of ultraviolet radiation exposes that air to ultraviolet radiation as that air contacts the at least one baffle 40, thus extending time that air is exposed to the ultraviolet radiation. The at least one first sensor 30, the at least one second sensor 34, and the at least one third sensor 36 sample air as air flows through plenum 12. The controller 32 varies the fan 26 speed to modify amount of time air is exposed to the ultraviolet radiation based on readings of the at least one first sensor 30. If the at least one second sensor 34 detects unacceptable air quality, the controller 32 provides the second signal to a display, controller, or any other element in comprising the system 5 on the vehicle 16 as is appropriate. That second signal can alert an interested party, such as a user of the vehicle, a manager of the vehicle 16, and the like that contamination associated with air about the vehicle 16 has been detected. If the at least one third sensor 36 detects an undesirable particulate or undesirable particulate amount, the third sensor 36 sends the third signal to the controller 32. Responsive to the third signal, the controller 32 provides an alert to an interested party, such as an operator of the vehicle 16 and the like, indicating particulate presence in the air.

What is claimed is:

1. A method for isolating and filtering respiration of an occupant of a vehicle, the vehicle having an interior and a seat disposed on the interior of the vehicle, a filtration system disposed on the seat for isolating and filtering respiration of the occupant, the filtration system having a plenum including an interior, a vent through which air enters at least one first duct, the least one first duct attached to the plenum, at least one second duct connected to the plenum, the at least one second duct separating the air from a first occupant from air from a second occupant, a source of ultraviolet radiation disposed in the plenum for reducing contaminate in the air, an at least one first sensor disposed on the interior of the plenum for monitoring carbon dioxide content of the air adjacent the at least one first sensor, an at least one second sensor disposed on the interior of the plenum for monitoring quality of the air adjacent the at least one second sensor, an at least one third sensor disposed on the interior of the plenum for monitoring the air adjacent the at least one third sensor for a particulate, a controller connected with the at least one first sensor which sends a first signal to the controller, the at least one second sensor which sends a second signal to the controller, and the at least one third sensor which sends a third signal to the controller, and a fan disposed on the interior of the plenum for increasing temporal duration of air exposure to ultraviolet radiation, the method comprising steps of:

energizing the source of ultraviolet radiation to sterilize in the air;

sampling the air adjacent the at least one first sensor to detect carbon dioxide content of that air;

sampling the air adjacent to the at least one second sensor to detect quality of that air;

sampling the air adjacent to the at least one third sensor to detect particulate in that air;

comparing result from the at least one first sensor to baseline carbon dioxide reading recorded in controller;

adjusting the fan speed to increase the temporal duration of the air exposure to ultraviolet radiation;

comparing result from the at least one second sensor with baseline air quality recorded in the controller;

sending a signal to a display comprising the filtration system to identify contaminate in the air;

comparing result from the at least one third sensor with baseline particulate recorded in controller; and sending an alert to an interested party indicating particulate presence in the air.

2. The method as defined in claim 1 wherein the ultraviolet radiation has a wavelength within a range of 100 nanometers to 280 nanometers.

3. The method as defined in claim 1 wherein the plenum comprises at least one baffle, the method further comprising steps of:

positioning the at least one baffle at a location empirically determined to increase surface area within the plenum exposed to ultraviolet radiation;

positioning the at least one baffle to collect an item, such as a respiration droplet and the like, from air about the at least one baffle; and sanitizing a surface of the a least one baffle with ultraviolet radiation.

4. The method as defined in claim 1 wherein an at least one third duct is connected to the interior of the plenum conveying air from the interior of the plenum to the interior of the vehicle.

\* \* \* \* \*